United States Patent [19]
Leavitt et al.

[11] Patent Number: 5,712,103
[45] Date of Patent: Jan. 27, 1998

[54] DIAGNOSTIC ASSAY FOR THE PREDICTION OF PREECLAMPSIA

[75] Inventors: John Leavitt, Palo Alto; Robert N. Taylor, San Francisco; Madhu Varma, Mountain View; Simon Shorter, Los Gatos, all of Calif.

[73] Assignee: Regents of the University of California, Oakland, Calif.

[21] Appl. No.: 388,251

[22] Filed: Feb. 13, 1995

[51] Int. Cl.$^6$ .................. G01N 33/53; G01N 33/537; G01N 33/543

[52] U.S. Cl. .................. 435/7.92; 435/7.8; 435/69.6; 514/8; 514/3

[58] Field of Search .................. 435/7.92, 69.6, 435/7.8; 514/8, 3

[56] References Cited

U.S. PATENT DOCUMENTS

| | | | |
|---|---|---|---|
| 4,134,792 | 1/1979 | Boguslaski et al. | 195/99 |
| 4,271,140 | 6/1981 | Bunting | 424/1 |
| 5,238,819 | 8/1993 | Roberts et al. | 435/29 |
| 5,554,504 | 9/1996 | Rutanen | 435/7.8 |
| 5,597,700 | 1/1997 | Konstantinov | 435/7.92 |

OTHER PUBLICATIONS

Chard et al., In: *Placental Function Tests*, Berlin, Springer-Verlag Not included Received (1982).

de Groot, Christianne, J.M. et al. "Midpregnancy Plasma IGFBP-1 And CA-125 Concentrations Reflect Impaired Trophoblastic Invasion Of Decidual Stroma In Women Destined To Develop Preeclampsia" *Society for Gynecologic Investigation Abstract Form* (1993).

Diagnostic Systems Laboratories Inc., 445 Medical Center Blvd., Webster, Texas 77598, Catalog No. DSL-7200, Active™ IGFBP-1 Coated-Tube Immunoradiometric Assay (IRMA) Kit for the Quantitative Measurement of Insulin–Like Growth Factor Binding Protein–1 in Serum. 1–16 7200 Jul. 28, 1994.

Howell et al., *Acta Obstet. et. Gynecol. Scand.*, 68:237–240 (1989).

Howell, R.J.S. et al., *British Journal of Obstetrics and Gynecology*, 92:1141 (1985).

Iino et al., *Obstet. Gynecol.* 68:58–60 (1986).

Lindberg et al. *J. Obstet. Gynecol. Br. Commonw.*, 80:1046–1053 (1973).

Rutanen, E–M. et al. *Int. J. Gynecol. Obstet.* 39:3 (1992).

Rutanen et al. *Am. J. Obst. Gyn.*, 144:460–463 (1982).

Rutanen et al. *Acta Endocrinol (Copenh)*, 123:7 (1990).

Schröcksnadel et al., *Geburtsh. U. Frauenheilk*, 52:332–334 (1992).

Spellacy et al. *Am. J. Obstet. Gynecol.*, 109:588–98 (1971).

Than et al., *IRCS Medical Science*, 11:627–628 (1983).

Than et al. *Arch. Gynecol.*, 236:41–45 (1984).

Wang, H.S. et al., *Journal of Endocrinology* 133:149 (1992).

Wang et al. *J. Endocrinol.*, 128:161–168 (1991).

Harlow, Ed. et al; 1988, Antibodies: A Laboratory Manual pp. 570–573.

Westwood, M et al, *J. Clin. Endocrin. and Metabolism*, vol. 79(6), 1994, pp. 1735–1741.

*Primary Examiner*—James C. Housel
*Assistant Examiner*—Ginny Allen Portner
*Attorney, Agent, or Firm*—Townsend and Townsend and Crew LLP

[57] ABSTRACT

The present invention provides methods and diagnostic kits for the detection or prediction of preeclampsia. More particularly, the present invention provides for the diagnosis of preeclampsia before the third trimester of pregnancy by detecting reduced levels of Insulin-like Growth Factor Binding Protein 1 (IGFBP-1) in maternal blood.

22 Claims, No Drawings

DIAGNOSTIC ASSAY FOR THE PREDICTION OF PREECLAMPSIA

FIELD OF THE INVENTION

This invention relates to an assay to detect or predict the onset of preeclampsia in pregnant women. More specifically, this invention provides for an assay that identifies pregnant women at high risk for preeclampsia by measuring the levels of Insulin-like Growth Factor Binding Protein-1 (IGFBP-1) in biological samples obtained during the first or second trimester of pregnancy.

BACKGROUND OF THE INVENTION

Preeclampsia is an idiopathic, life-threatening disease of late pregnancy in which hypertension is associated with hepatic, neurologic, hematologic, or renal involvement. Rapid development of edema, particularly of the ankles, face and hands, along with a rise in blood pressure, usually signals the onset of this condition. Jaundice and abnormal liver function may be present.

When preeclampsia occurs in a hypertensive patient, a rapid acceleration of the blood pressure elevation is accompanied by an increase in proteinuria, oliguria, edema, and coagulopathy. This is a life threatening syndrome and tends to recur with future pregnancies. In the postpartum period, proteinuric patients are particularly susceptible to the development of postpartum renal failure. Preeclampsia is often characterized by hyperreflexia, visual disturbances and headache indicating neurologic involvement which may ultimately progress to eclampsia characterized by convulsions. Preeclampsia occurs in 7–10% of pregnancies and is responsible for significant maternal and fetal morbidity (Roberts, *Pregnancy-related hypertension.*, pages 703–752 In *Maternal-Fetal Medicine-Principles and Practice*, Creasy & Resnick, eds., W. B. Saunders, Philadelphia (1984).

Once preeclampsia is diagnosed, hospitalization is indicated, since, as indicated above, the disease can rapidly progress to eclampsia, characterized by convulsions resulting in significant maternal and fetal trauma. The definitive treatment of preeclampsia and eclampsia is delivery of the conceptus, which is carried out promptly, if fetal size and maturity are adequate. If the fetus is immature, management consists of bed rest in a quiet environment and control of neurologic manifestations and blood pressure, the former with magnesium sulfate and the latter usually with vasodilators such as hydralazine and methyldopa. Early detection of preeclampsia and implementation of appropriate therapeutic measures greatly reduces maternal and fetal morbidity. The long term prognosis of promptly detected preeclampsia is generally favorable.

Despite decades of interest and research, the pathogenesis of this disease is still poorly understood. In recent years, however, the availability of the measurement of placental proteins opened new perspectives in the diagnosis of fetoplacental dysfunction. In particular, placental proteins have attracted interest as diagnostic markers of various pathologies during pregnancy. Thus, for example, a decrease in the maternal serum concentration of pregnancy-specific beta-1-glycoprotein ($sp_1$) detected by serial measurements could predict fetal malnutrition (Csaba, *Med. Sci.*, 10:840–842 (1982); Karg et al. *Arch. Gynaekol*, 231:67–73 (1981).

Biochemical tests of fetoplacental well-being have been applied in the study of preeclampsia (Chard et al., pages 1–93 In: *Placental Function Tests*, Berlin, Springer-Verlag (1982)), sometimes with dramatic clinical significance (Lindberg, et al. *J. Obstet. Gynecol. Br. Commonw.*, 80:1046–1053 (1973); Spellacy et al. *Am. J. Obstet. Gynecol.*, 109:588–98 (1971)). In particular, one placental protein that has attracted recent interest in this context is Insulin-like Growth Factor Binding Protein-1 (IGFBP-1) formerly known as placental protein 12 (PP12).

IGFBP-1 is a major endometrial secretory protein produced by stromal cells during decidualization. A number of studies have demonstrated increased concentrations of PP12 (IGFBP-1) associated with preeclampsia (see, e.g. Howell, et al., *Acta. Obstet. Gynecol. Scand.*, 68:237–240 (1989); Iino et al., *Obstet. Gynecol.* 68:58–60 (1986); Than et al. *Arch. Gynecol.*, 236:41–45 (1984)). However, all of these studies measured IGFBP-1 levels during the third trimester after preeclampsia was manifest. They provide no data suggesting that alterations in levels of IGFBP-1 earlier in pregnancy (e.g. second trimester) are in any manner predictive or correlated to the late pregnancy manifestation of preeclamptic symptoms. Moreover, a more recent study concluded that IGFBP-1 was not a clinically usable parameter in the diagnosis of hypertensive disorders of pregnancy at term (Schröcksnadel et al., *Geburtsh. U. Faruenheilk*, 52:332–334 (1992)).

SUMMARY OF THE INVENTION

This invention relates to the discovery that pregnant women who ultimately develop preeclampsia show significantly lowered concentrations of IGFBP-1 in the first or second trimester as compared to pregnant women who never develop preeclampsia. In particular, the reduction of IGFBP-1 levels in blood or cervicovaginal secretions provides a diagnostic marker predictive of the ultimate onset preeclampsia. Thus, in a preferred embodiment, this invention provides for a diagnostic assay for the prediction of preeclampsia. The assay includes the steps of collecting a biological sample, more preferably a blood sample or a sample of cervicovaginal secretions comprising IGFBP-1, from a pregnant female human and detecting the concentration of Insulin-like Growth Factor Binding Protein-1 (IGFBP-1) in the sample, where a reduced concentration of IGFBP-1 in the sample as compared to the IGFBP-1 concentration in a sample from a healthy pregnant woman predictive of the development of preeclampsia. The sample is preferably collected before the third trimester of pregnancy, more preferably in the second trimester of pregnancy and most preferably at the mid second trimester. The patient may be a patient having a preexisting hypertensive condition, or may be a patient that shows normal prepregnancy blood pressure. Detection of the IGFBP-1 concentration may involve the binding of IGFBP-1 by an antibody that specifically binds IGFBP-1. The antibody may be a polyclonal or a monoclonal antibody. In addition, the antibody may be an intact antibody or an antibody fragment.

In one particularly preferred embodiment, the detection of IGFBP-1 is by a sandwich assay. The sandwich assay involves providing, immobilized on a substrate a first antibody that specifically binds IGFBP-1 contacting the sample with the first antibody thereby forming an antibody/IGFBP-1 complex with IGFBP-1 present in the sample; providing a second antibody that specifically binds it when IGFBP-1 is bound by the first antibody; and detecting the amount of second antibody associated with said IGFBP-1/antibody complex. The second antibody may be labeled in which case detecting comprises detecting the amount of label associated with the IGFBP-1/antibody complex. Alternatively, detecting may involve contacting the second antibody with a labeled third antibody that binds the second antibody and detecting the amount of labeled third antibody associated with the second antibody immobilized on the substrate.

In another preferred embodiment, the detection of IGFBP-1 is by a competitive assay. This assay involves providing a first antibody that specifically binds IGFBP-1; contacting the first antibody with a labeled IGFBP-1 and the sample; and detecting the amount of labeled IGFBP-1 that forms an IGFBP-1/antibody complex. The first antibody may be attached to a substrate. The amount of antibody forming the IGFBP-1/antibody complex may be determined by detecting the labeled IGFBP-1 present in the IGFBP-1/antibody complex. Alternatively, the amount of antibody forming the IGFBP-1/antibody complex may be determined by detecting the labeled IGFBP-1 that is not immobilized.

In yet another preferred embodiment, the detection of IGFBP-1 is by a hapten inhibition assay. This assay involves contacting the sample with a first antibody that specifically binds an IGFBP-1 endogeneous in the sample thereby forming a first IGFBP-1/antibody complex. The sample containing the antibody is then contacted to an IGFBP-1 immobilized on the substrate such that antibody in the sample that is not complexed with the endogenous IGFBP-1 binds the immobilized IGFBP-1 thereby forming a second IGFBP-1/antibody complex. The amount of first antibody not bound by the endogenous IGFBP-1 is then detected. The amount of first antibody not bound by the IGFBP-1 endogenous in the sample may be determined by detecting either the amount of first IGFBP-1/antibody complex or the amount of second IGFBP-1/antibody complex.

In a particularly preferred embodiment, the first antibody is labeled. Alternatively, the antibody may be detected by contacting it with a labeled second antibody that specifically binds the first antibody.

In still yet another preferred embodiment, the detection of IGFBP-1 is by a Western Blot utilizing an antibody that specifically binds IGFBP-1.

In another embodiment, a maternal blood plasma concentration of IGFBP-1 ranging from about 75 ng/ml to about 25 ng/ml, more preferably less than about 60 ng/ml at mid second trimester is predictive of preeclampsia.

In all of the above-described assays, the label may be a radioactive label, an enzymatic label, a colorimetric label, or a fluorescent label. In addition, the assays may additionally include a step to eliminate non-specific binding. This step may involve contacting the substrate with a protein such as bovine serum albumin (BSA), gelatin, or nonfat powdered milk.

The present invention also provides for kits for the detection and prediction of preeclampsia. A preferred kit comprises an antibody capable of specifically binding Insulin-like Growth Factor Binding Protein-1 (IGFBP-1) in a human blood sample and instructional materials teaching the use of the antibody in an assay for the detection of a predilection to preeclampsia. The kit may also include one or more of the following: concentration standards of IGFBP-1, a negative IGFBP-1 control, a labeled antibody at specifically binds IGFBP-1, a labeled antibody that specifically binds an anti-IGFBP-1 antibody, buffers, and blocking proteins such as bovine serum albumin or nonfat powdered milk. The labels on the antibodies are selected from the group consisting of a radioactive label, an enzymatic label, a colorimetric label, and a fluorescent label.

Definitions

The following definitions are set forth to illustrate and define the meaning and scope of the various terms used to describe the invention herein.

The term "IGFBP-1" is used herein to refer to Insulin-like Growth Factor Binding Protein 1 as it is commonly known to those of skill in the art. Thus, assays that detect IGFBP-1 are intended to detect the level of endogenous (native) IGFBP-1 present in the maternal blood. However, exogenous IGFBP-1 (IGFBP-1 from a source extrinsic to the blood sample) may be added to various assays to provide a label or to compete with the native IGFBP-1 in binding to an anti-IGFBP-1 antibody. One of skill will appreciate that an IGFBP-1 mimetic may be used in place of exogenous IGFBP-1 in this context. An "IGFBP-1 mimetic", as used herein, refers to a molecule that bears one or more IGFBP-1 epitopes such that it is specifically bound by an antibody that specifically binds native IGFBP-1.

The phrase "predictive of preeclampsia" is used herein to refer to a marker or assay that predicts the ultimate onset of preeclampsia. However, it will be appreciated by one of skill in the art, that all assays exhibit a certain level of false positives and false negatives. Even where a positive result in an assay is not invariably associated with the ultimate onset of preeclampisa (i.e. where there are some false positives), the result is valuable as it results in more careful monitoring of the patient during pregnancy for the manifestation of preeclampitic symptoms thus leading to early identification of a preeclamptic pregnancy. Thus, "predictive of preeclampsia" as used herein also refers to the identification of individuals predisposed to, or at high risk for, the ultimate development of preeclampsia. An assay is predictive of preeclampsia where detection of the assay marker (e.g. lowered IGFBP-1) shows a statistically significant association or correlation with the ultimate manifestation of symptoms of preeclampsia.

The term "blood sample" as used herein includes whole blood or derivatives of whole blood well known to those of skill in the art. Thus a blood sample includes the various fractionated forms of blood such as plasma or serum and whole or fractionated blood additionally comprising various diluents as may be added to facilitate storage or processing in a particular assay. Such diluents are well known to those of skill in the art and include various buffers, anticoagulants, preservatives and the like.

As used herein, an "immunoassay" is an assay that utilizes an antibody to specifically bind to the analyte. The immunoassay is characterized by the use of specific binding to a particular antibody as opposed to other physical or chemical properties to isolate, target, and quantify the analyte.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies may exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially an Fab with part of the hinge region (see, *Fundamental Immunology*, W. E. Paul, ed., Raven Press, N.Y. (1993), which is incorporated herein by reference, for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies.

The phrase "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to a protein under such conditions may require an antibody that is selected for its specificity for a particular protein. For example, antibodies can be raised to the human IGFBP-1 protein that bind IGFBP-1 and not to any other proteins present in a blood sample. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, N.Y., for a description of immunoassay formats and conditions that can be used to determine specific immunoreactivity.

A "concentration standard" is a predetermined concentration of a particular moiety, in this case IGFBP-1, that is used for standardizing an assay for that moiety. A negative control, is a sample that lacks any of the specific analyte the assay is designed to detect and thus provides a reference baseline for the assay.

DESCRIPTION OF THE PREFERRED EMBODIMENT

This invention involves the discovery that pregnant women who ultimately develop preeclampsia show lowered maternal blood concentrations of Insulin-like Growth Factor Binding Protein-1 (IGFBP-1) in the second trimester as compared to pregnant women who never develop preeclampsia. In particular, mid-trimester plasma IGFBP-1 concentrations are significantly lower in women in whom preeclampsia develops 12 to 26 weeks later as compared to matched patients with normal pregnancy outcomes. Sampling at a mean gestational age of 18±1 weeks is highly correlated with diagnostic signs and symptoms appearing in preeclamptic patients about 21±1 weeks later.

The correlation between reduced mid-trimester plasma IGFBP-1 and the ultimate onset of preeclampsia is highly significant (p<0.05). In addition, IGFBP-1 concentrations at mid second trimester (approximately week 18) differ by as much as a factor of two or more between healthy and ultimately preeclamptic patients, with preeclamptic patients showing the lower midtrimester IGFBP-1 concentrations. The concentration differences are easily detected using routine assays, and thus IGFBP-1 provides a useful diagnostic marker for the prediction of preeclampsia.

Although altered IGFBP-1 levels have been associated with preeclampsia, it is a surprising discovery of the present invention that IGFBP-1 is a suitable predictive marker for preeclampsia. In light of previous studies it is particularly surprising that preeclampsia is predicted by reduced IGFBP-1 concentrations. Than et al., *Arch. Gynecol.*, 236:41–45 (1984), Iino et al. *Obstet. Gynecol*, 68:58 (1986), and Howell, et al. *Acta Obstet. et. Gynecol. Scand.*, 68:237–240 (1989), independently report elevated levels of PP12 in the third trimester of patients manifesting symptoms of preeclampsia. Schröcksnadel et al., *Geburtsh. U. Faruenheilk*, 52:332–334 (1992) also showed elevated levels of PP12 in hypertensive pregnant women, but concluded that because of a widespread range of results "PP12 does not seem to be a clinically usable parameter in the diagnosis of hypertensive disorders of pregnancy" (see abstract).

In contrast to the previous studies that focused on elevated IGFBP-1 levels after preeclamptic symptoms manifested (typically in third trimester) the present invention relies, in part, on the unexpected discovery that depressed IGFBP-1 levels during the second trimester are predictive of preeclampsia.

Without being bound to a particular theory, it is believed that the lowered IGFBP-1 levels during the second trimester are associated with reduced trophoblastic migration into the maternal decidua during the first half of pregnancy. IGFBP-1 is a major endometrial secretory protein whose primary source in pregnancy appears to be decidual stromal cells. The reduced trophoblastic migration into the maternal decidual and the concomitant reduced production of IGFBP-1 suggests that the etiology of preeclampsia involves defective decidual stromal cell-cytotrophoblast interactions.

Characteristics of IGFBP-1

Insulin-like Growth Factor Binding Protein-1 (IGFBP-1, formerly called PP12) is one of six structurally related proteins which specifically bind and modulate the bioactivity of the mitogenic peptides, IGF-I and IGF-II (Lee et al. *Proc. Soc. Exp. Biol. Med.*, 204:4–29 (1993). The mature IGFBP-1 is a 25.3 kDA protein synthesized primarily in liver and decidualized uterine endometrium. Low levels of synthesis may also occur in luteal-phase granulosa cells and in non-human primate and rodent kidney. In vitro, IGFBP-1 synthesis has been identified in continuous human cell lines derived from liver (HepG2), breast I(MDA-MB-231 and Hs578t) and uterine endometrium (HEC1B and KLE) (Lee, supra, Lee et al. *Mol. Endocrinol.*, 2:404–411 (1988), Yee et al. *Breast Canc. Res. Treat.*, 18:3–10 (1991) and Pekonen et al., *Mol. Cell. Endocrinol.*, 75:81–87 (1991).

IGFBP-1 levels are high in amniotic fluid and fetal serum, and serum levels decline with age during postnatal life (Hall et al. *Acta Endocrinol (Copenh)*, 118:321–326 (1988). Elevated IGFBP-1 serum levels have been identified in pregnancy, renal failure, malnutrition, insulin-deficiency (e.g. insulin-dependent diabetes mellitus) and liver cirrhosis and carcinoma (Lee et al. *Proc. Soc. Exp. Biol. Med.*, 204:4–29 (1993). Serum IGFBP-1 levels in normal individuals and in individuals with growth hormone deficiency vary considerably in relation to meals. Levels increase 2- to >20-fold after an overnight fast and show an exponential fall following a meal. Studies indicate that these changes are directly related to insulin concentrations and not growth hormone or glucose (Conover et al. *Diabetes*, 39:1251–1256 (1990), Lee et al. *Metabolism*, 42:409–414 (1993)).

In light of the insulin-dependent variation in IGFBP-1 concentration, one of skill in the art will recognize that diagnostic assays utilizing IGFBP-1 may provide greater accuracy when controlled for insulin levels. Means of controlling for insulin level during an assay are well known in the art and include, but are not limited to, requiring a preassay fast, simultaneous assay of covarying insulin levels, and the like. Similarly, diurnal variations in IGFBP-1 may be avoided by drawing blod samples between 0900 and 2000 hours.

Assays for IGFBP-1

Sample Collection and Processing

IGFBP-1 is preferably quantified in a biological sample derived from a patient. As used herein, a biological sample is a sample of biological tissue or fluid that contains an IGFBP-1 concentration that may be correlated with blood levels of IGFBP-1. Particularly preferred biological samples include blood and cervicovaginal secretions. Cervicovaginal secretions have been shown to contain endometrial-secreted proteins at levels that may be closely correlated with endometrial and blood levels of those proteins. See, for example, U.S. Pat. No. 5,096,830, incorporated herein by reference, which describes cervicovaginal secretions as diagnostic assay samples, and provides means for taking such samples.

In another preferred embodiment, IGFBP-1 is quantified in whole blood or blood derivatives such as blood plasma or blood serum. Blood samples are isolated from a patient according to standard methods well known to those of skill in the art, most typically by venipuncture. Although the sample is typically taken from a human patient, the assays can be used to detect IGFBP-1 in samples from any mammal, such as dogs, cats, sheep, cattle, and pigs.

The sample may be pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

In a preferred embodiment, assays are performed using blood plasma (blood lacking a cellular component) or blood serum (blood lacking a cellular component and clotting factors). Means of preparing blood plasma are well known to those of skill in the art and typically involve centrifugation or filtration to produce blood plasma, or clotting followed by centrifugation or filtration to produce blood serum. The blood plasma or serum may be diluted by the addition of buffers or other reagents well known to those of skill in the art and may be stored for up to 24 hours at 2°–8° C., or at −20° C. or lower for longer periods, prior to measurement of IGFBP-1.

Quantification of IGFBP-1.

IGFBP-1 may be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay(RIA), enzyme-linked immunosorbent assays (ELISAs), immunofluorescent assays, western blotting, and the like.

As used herein, an immunoassay is an assay that utilizes an antibody to specifically bind to the analyte. The immunoassay is characterized by the use of specific binding to a particular antibody as opposed to other physical or chemical properties to isolate, target, and quantify the analyte.

Immunological Binding Assays

In a preferred embodiment, IGFBP-1 is detected and quantified using any of a number of well recognized immunological binding assays. (See for example, U.S. Pat. Nos. 4,366,241; 4,376,110; 4,517,288; and 4,837,168, which are hereby incorporated by reference.) For a review of the general immunoassays, see also *Methods in Cell Biology Volume* 37: *Antibodies in Cell Biology*, Asai, ed. Academic Press, Inc. N.Y. (1993); *Basic and Clinical Immunology* 7th Edition, Stites & Terr, eds. (1991), which are hereby incorporated by reference.

Immunological binding assays (or immunoassays) typically utilize a "capture agent" to specifically bind to and often immobilize the analyte (in this case IGFBP-1). The capture agent is a moiety that specifically binds to the analyte. In a preferred embodiment, the capture agent is an antibody that specifically binds IGFBP-1.

The antibody may be provided by any of a number of means well known to those of skill in the art (see, e.g. *Methods in Cell Biology Volume* 37: *Antibodies in Cell Biology*, Asai, ed. Academic Press, Inc. N.Y. (1993); and *Basic and Clinical Immunology* 7th Edition, Stites & Terr, eds. (1991), which are hereby incorporated by reference). The antibody may be a whole antibody or an antibody fragment. It may be polyclonal or monoclonal, and it may be produced by challenging an organism (e.g. mouse, rat, rabbit, etc.) with IGFBP-1 or an epitope derived therefrom. Alternatively, the antibody may be produced de novo using recombinant DNA methodology.

Antibodies that specifically bind IGFBP-1 may be produced using standard methods well known to those of skill in the art or may be obtained commercially. For example, Diagnostic Systems Laboratories, Inc. (Webster, Tex., USA) produces an immunoradiometric assay kit for the measurement of IGFBP-1. This kit contains immobilized anti-IGFBP-1 in addition to other reagents useful for assaying IGFBP-1.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled IGFBP-1 or a labeled anti-IGFBP-1 antibody. Alternatively, the labeling agent may be a third moiety, such as another antibody, that specifically binds to the antibody/IGFBP-1 complex.

In a preferred embodiment, the labeling agent is an antibody that specifically binds to the capture agent (anti-IGFBP-1). Such agents are well known to those of skill in the art, and most typically comprise labeled antibodies that specifically bind antibodies of the particular animal species from which the capture agent is derived. Thus, for example, where the capture agent is a mouse derived anti-human IGFBP-1 antibody, the label agent may be a goat anti-mouse IgG; an antibody that is specific to the constant region of the mouse antibody.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species. See, generally Kronval, et al., *J. Immunol.*, 111:1401–1406 (1973), and Akerstrom, et al., *J. Immunol.*, 135:2589–2542 (1985).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting IGFBP-1 may be either competitive or noncompetitive. Noncompetitive immunoassays are assays in which the amount of captured analyte (in this case IGFBP-1) is directly measured. In one preferred "sandwich" assay, for example, the capture agent (anti-IGFBP-1 antibodies) can be bound directly to a solid substrate where they are immobilized. These immobilized antibodies then capture IGFBP-1 present in the test sample. The IGFBP-1 thus immobilized is then bound by a labeling agent, such as a second human IGFBP-1 antibody bearing a label. Alternatively, the second IGFBP-1 antibody may lack a label, but it may, in turn, be bound by a labeled third antibody specific to antibodies of the species from which the second antibody is derived.

Sandwich assays are particularly preferred as diagnostics for the present invention. A sandwich assay for IGFBP-1 is commercially available (e.g. Diagnostic Systems Laboratories, Webster, Tex., USA). The commercial assay provides immobilized anti-IGFBP-1, IGFBP-1 concentration standards, $^{125}$I labeled anti-IGFBP-1, and positive and negative IGFBP-1 controls. As described above, the immobilized anti-IGFBP-1 specifically binds to IGFBP-1 present in the sample. Then the $^{125}$I labeled anti-IGFBP-1 binds to the already bound IGFBP-1. Free $^{125}$I labeled anti-IGFBP-1 is washed away and the remaining bound $^{125}$I labeled anti-IGFBP-1 is detected using a gamma detector.

Competitive Assays

In competitive assays, the amount of analyte (IGFBP-1) present in the sample is measured indirectly by measuring the amount of an added (exogenous) analyte (IGFBP-1) displaced (or competed away) from a capture agent (anti IGFBP-1 antibody) by the analyte present in the sample. In one competitive assay, a known amount of in this case IGFBP-1 is added to the sample and the sample is then contacted with a capture agent, in this case an antibody that specifically binds IGFBP-1. The amount of IGFBP-1 bound to the antibody is inversely proportional to the concentration of IGFBP-1 present in the sample.

In a particularly preferred embodiment, the antibody is immobilized on a solid substrate. The amount of IGFBP-1 bound to the antibody may be determined either by measuring the amount of IGFBP-1 present in an IGFBP-1/ antibody complex, or alternatively by measuring the amount of remaining uncomplexed IGFBP-1. The amount of IGFBP-1 may be detected by providing a labeled IGFBP-1.

A hapten inhibition assay is another preferred competitive assay. In this assay a known analyte, in this case IGFBP-1 is immobilized on a solid substrate. A known amount of anti-IGFBP-1 antibody is added to the sample, and the sample is then contacted with the immobilized IGFBP-1. In this case, the amount of anti-IGFBP-1 antibody bound to the immobilized IGFBP-1 is proportional to the amount of IGFBP-1 present in the sample. Again the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Reduction of Non-Specific Binding

One of skill in the art will appreciate that it is often desirable to reduce non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin are widely used with powdered milk being most preferred.

Other Assay Formats

Western blot (immunoblot) analysis can also be used to detect and quantify the presence of IGFBP-1 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind IGFBP-1. The anti-IGFBP-1 antibodies specifically bind to IGFBP-1 on the solid support. These antibodies may be directly labeled or alternatively may be subsequently detected using labeled antibodies (e.g. labeled sheep anti-mouse antibodies) that specifically bind to the anti-IGFBP-1.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.* 5:34–41 (1986), which is incorporated herein by reference.

Labels

The particular label or detectable group used in the assay is not a critical aspect of the invention, so long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, and the like), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions..

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labelling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Substrates

As mentioned above, depending upon the assay, various components, including the antigen, target antibody, or antihuman antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass or plastic bead. The desired component may be covalently bound or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, are included substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials may be employed, particularly as laminates, to obtain various properties. For example, protein coatings, such as gelatin can be used to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes*, Ichiro Chibata, Halsted Press, N.Y., 1978, and Cuatrecasas, *J. Biol. Chem.* 245 3059 (1970) which are incorporated herein by reference.

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as Concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082, which are incorporated herein by reference.

Determination of IGFBP-1 Levels for Prediction of Preeclampsia

The preeclamptic condition is predicted by a statistically significant decrease in the concentration of IGFBP-1 in maternal blood by the mid second trimester of pregnancy. Lowered IGFBP-1 levels precede the appearance of preeclamptic symptoms by approximately 12 to 26 weeks. Thus, IGFBP-1 levels provide an advantageous diagnostic of preeclampsia.

As indicated above, blood levels of IGFBP-1 vary with the physiological state of the patient. Thus, in healthy pregnant women, serum IGFBP-1 levels begin to increase during the first trimester of pregnancy to peak at the second trimester when decidualization is strongest. Rutanen et al. *Acta Endocrinol (Copenh)*, 123:7 (1990); Rutanen et al. *Am. J. Obst. Gyn.*, 144:460–463 (1982); Than et al., *IRCS Medical Science*, 11:627–628 (1983); Wang et al. *J. Endocrinol.*, 128:161–168 (1991). In addition, as explained above, blood levels of IGFBP-1 may vary with insulin levels.

Nevertheless, baseline healthy levels of IGFBP-1 and levels indicative of preeclampsia may be determined by means well known to those of skill in the art. Generally this simply involves routine screening of healthy patients and patients that ultimately develop preeclampsia. IGFBP-1 variation determined by time of gestation may be controlled by sampling uniformly at approximately the same gestational period, or alternatively, by determining blood IGFBP-1 levels as a function of period of gestation.

In addition, in order to decrease variability in the assay, one may also control for variation associated with insulin level. Means of controlling for such variation are well known to those of skill in the art. IGFBP-1 undergoes rapid in vivo metabolism and clearance, with a $T_{1/2}$ estimated at 8 to 12 minutes (Lewitt et al., *Endocrinol.*, 124:2254–2256 (1991)). Thus, IGFBP-1 levels rapidly fall following a meal. In view of the rapid clearance of IGFBP-1, optimization of variables in IGFBP-1 detection may be accomplished by blood sampling after a normal overnight fasting period (this would not be detrimental to the fetus). Alternatively, the covariation of IGFBP-1 levels with insulin could be determined and a simultaneous assay for both insulin and IGFBP-1 would allow correction back to a baseline IGFBP-1 level.

The differences in IGFBP-1 level at mid second trimester between healthy pregnant women and women that ultimately manifest symptoms of preeclampsia are so great (typically a factor of 2 or more) that differences are readily detected. Optional controls for insulin levels simply decrease the variability in the assay.

Diagnostic Kits for Detection or Prediction of Preeclampsia

The present invention also provides for kits for the diagnosis of women at risk for preeclampsia. The kits preferably include an antibody that specifically binds to IGFBP-1. The antibody may be free or immobilized on a solid support such as a test tube, a microtiter plate, a dipstick and the like. The kit may also contain instructional materials teaching the use of the antibody in an assay for the detection of a predilection to preeclampsia.

Additionally, the kit may contain a second antibody that specifically binds IGFBP-1. The second antibody may be labeled, or alternatively, the kit may contain a labeled third antibody that specifically binds the second antibody. The kit may also contain appropriate control series of IGFBP-1, buffer solutions, positive and negative controls, washing solutions, dilution buffers and the like for the preparation and analysis of IGFBP-1 in blood.

The following example illustrates the functionality of the invention described herein. The example is not to be construed as a limitation on the claims. It is further understood that non-critical variations in procedures by those of skill are possible.

EXAMPLE 1

A nested longitudinal case-control study was used to address the hypothesis that trophoblastic invasion and remodelling of the endometrium in pregnancies destined for preeclampsia affect the maternal vascular deportation of decidual cell proteins, in particular IGFBP-1. In particular, maternal blood IGFBP-1 levels were compared between women undergoing normal healthy pregnancies and women destined to manifest preeclamptic symptoms. All samples were drawn between 0800 and 2100 h thus avoiding the nocturnal peak of IGFBP-1 concentrations.

Radioimmunoassay data from 10 preeclamptic and 10 matched normal controls (expressed as mean±SE) were analyzed using 2-factor ANOVA with Bonferroni corrections to compare pregnancy outcomes and decidual protein concentrations in each trimester of pregnancy.

Midtrimester plasma IGFBP-1 concentrations were significantly lower in women in whom preeclampsia developed 12–26 weeks later compared to matched patients with normal pregnancy outcomes (49±8 vs. 118±24 ng/ml, respectively, P=0.05). The mean gestational age at the time of drawing of the second trimester plasma samples was 18±1 weeks for both preeclamptic and control women (P=0.99). Diagnostic signs and symptoms in the 10 preeclamptic patients appeared 21±1 weeks from the time of midtrimester plasma sampling. The findings provide biochemical evidence that abnormalities of midtrimester placentation in preeclampsia involve defective decidual stromal cell-cytotrophoblast interactions. The 21-week interval between detection of low plasma IGFBP-1 concentrations and the onset of clinical signs of preeclampsia suggests that serial quantification of maternal IGFBP-1 levels provides a predictive test to define women at risk for this syndrome.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed is:

1. A diagnostic immunoassay for the prediction of preeclampsia, said assay comprising the steps of:
   (a) collecting a plasma sample from a pregnant female human during the second trimester of pregnancy; and
   (b) detecting the concentration of Insulin-like Growth Factor Binding Protein-1 (IGFBP-1) in said sample by an immunological means;
       wherein a reduced concentration of IGFBP-1 in said sample, as compared to the IGFBP-1 concentration in a plasma sample from a healthy pregnant women at the same gestational stage, is predictive of preeclampsia.

2. The assay of claim 1, wherein said plasma sample is collected from a patient that has normal prepregnancy blood pressure.

3. The assay of claim 1, wherein said detecting comprises the binding of IGFBP-1 by an antibody that specifically binds IGFBP-1.

4. The assay of claim 1, wherein said immunological means uses a monoclonal antibody.

5. The assay of claim 1, wherein said detecting comprises an antigen sandwich assay, said assay comprising the steps of:
   (a) providing, immobilized on a substrate, a first antibody that specifically binds IGFBP-1;
   (b) contacting said blood sample with said first antibody, thereby forming an IGFBP-1/antibody complex with IGFBP-1 present in said blood sample;
   (c) providing a second antibody that specifically binds IGFBP-1 when IGFBP-1 is bound by said first antibody;
   (d) detecting the amount of second antibody associated with said IGFBP-1/antibody complex.

6. The assay of claim 5, wherein said second antibody is labeled and said detecting comprises detecting the amount of label associated with said IGFBP-1/antibody complex.

7. The assay of claim 6, wherein said label is selected from the group consisting of a radioactive label, an enzymatic label, a colorimetric label, and a fluorescent label.

8. The assay of claim 5, wherein said detecting comprises:
   contacting said second antibody with a labeled third antibody that binds said second antibody; and
   detecting the amount of labeled third antibody associated with said second antibody immobilized on said substrate.

9. The assay of claim 8, wherein said label is selected from the group consisting of a radioactive label, an enzymatic label, a colorimetric label, and a fluorescent label.

10. The assay of claim 1, wherein said detecting comprises a competitive assay, said assay comprising the steps of:

(a) providing a first antibody that specifically binds IGFBP-1;

(b) contacting said first antibody with a labeled IGFBP-1 and said sample; and (c) detecting the amount of labeled IGFBP-1 that forms an IGFBP-1/antibody complex.

11. The assay of claim 10, wherein said first antibody is immobilized on a solid substrate.

12. The assay of claim 10, wherein said detecting comprises detecting the labeled IGFBP-1 bound to said first antibody.

13. The assay of claim 11, wherein said detecting comprises detecting the labeled IGFBP-1 remaining unbound in solution.

14. The assay of claim 10, wherein said label is selected from the group consisting of a radioactive label, an enzymatic label, a colorimetric label, and a fluorescent label.

15. The assay of claim 1, wherein said detecting comprises a hapten inhibition assay, said assay comprising the steps of:

(a) providing, immobilized on a substrate, an IGFBP-1 protein;

(b) contacting said sample with a first antibody that specifically binds an IGFBP-1 endogenous in said sample thereby forming a first IGFBP-1/antibody complex;

(c) contacting said IGFBP-1 protein with said sample and first antibody where remaining unbound first antibody binds said immobilized IGFBP-1 thereby forming a second IGFBP-1/antibody complex; and (d) detecting the amount of first antibody not bound by the IGFBP-1 endogenous in the sample.

16. The assay of claim 15, wherein said detecting the amount of first antibody not bound by IGFBP-1 endogenous in the sample comprises detecting the first IGFBP-1/antibody complex.

17. The assay of claim 15, wherein said detecting the amount of first antibody not bound by IGFBP-1 endogenous in the sample comprises detecting the second IGFBP-1/antibody complex.

18. The assay of claim 15, wherein said first antibody is labeled.

19. The assay of claim 18, wherein said label is selected from the group consisting of a radioactive label, an enzymatic label, a colorimetric label, and a fluorescent label.

20. The assay of claim 15, wherein said detecting is by:

(a) contacting said immobilized first antibody with a labeled second antibody that binds said first antibody thereby immobilizing said second antibody; and (b) detecting the amount of immobilized label.

21. The assay of claim 20, wherein said label is selected from the group consisting of a radioactive label, an enzymatic label, a colorimetric label, and a fluorescent label.

22. The assay of claim 1, wherein said detecting comprises Western Blotting utilizing an antibody that specifically binds IGFBP-1.

* * * * *

UNITED STATES PATENT AND TRADEMARK OFFICE
CERTIFICATE OF CORRECTION

PATENT NO. : 5,712,103
DATED : January 27, 1998
INVENTOR(S) : John Leavitt et al.

It is certified that error appears in the above-identified patent and that said Letters Patent is hereby corrected as shown below:

<u>Title page,</u>
Item [73], Assignee, insert after "Regents of the University of California, Oakland, Calif.": -- Adeza Biomedical Corporation, Sunnyvale, Calif. --.

Signed and Sealed this

Fifteenth Day of July, 2003

JAMES E. ROGAN
*Director of the United States Patent and Trademark Office*